United States Patent
Lee et al.

(10) Patent No.: US 9,606,063 B2
(45) Date of Patent: Mar. 28, 2017

(54) EMBEDDED DEVICE FOR MEASURING COMPONENT AND COMPOSITION OF MULTI-PHASE FLOW FLUID FLOWING IN PIPE

(71) Applicant: KOREA INSTITUTE OF INDUSTRIAL TECHNOLOGY, Cheonan-si, Chungcheongnam-do (KR)

(72) Inventors: Ju Dong Lee, Busan (KR); Hyung Ho Jo, Busan (KR); Young Cheol Lee, Busan (KR); Joung Ha Kim, Cheonan-si (KR); Hyoung Chan Kim, Bucheon-si (KR); Kyung Chan Kang, Daegu (KR)

(73) Assignee: KOREA INSTITUTE OF INDUSTRIAL TECHNOLOGY, Cheonan-si, Chungcheongnam-Do (KR)

( * ) Notice: Subject to any disclaimer, the term of this patent is extended or adjusted under 35 U.S.C. 154(b) by 64 days.

(21) Appl. No.: 14/653,021

(22) PCT Filed: Dec. 18, 2013

(86) PCT No.: PCT/KR2013/011803
§ 371 (c)(1),
(2) Date: Jun. 17, 2015

(87) PCT Pub. No.: WO2014/098469
PCT Pub. Date: Jun. 26, 2014

(65) Prior Publication Data
US 2016/0003745 A1   Jan. 7, 2016

(30) Foreign Application Priority Data
Dec. 18, 2012 (KR) .................. 10-2012-0148961

(51) Int. Cl.
*G01N 21/65* (2006.01)
*G01N 33/28* (2006.01)
*G01N 21/85* (2006.01)

(52) U.S. Cl.
CPC ............. *G01N 21/65* (2013.01); *G01N 21/85* (2013.01); *G01N 33/2823* (2013.01)

(58) Field of Classification Search
CPC ...... G01J 3/44; G01N 21/65; G01N 2021/656
See application file for complete search history.

(56) References Cited

U.S. PATENT DOCUMENTS

| 4,802,761 A | 2/1989 | Bowen et al. |
| 5,751,415 A | 5/1998 | Smith et al. |

(Continued)

FOREIGN PATENT DOCUMENTS

| KR | 20110087206 | 8/2011 |
| KR | 20120031014 | 3/2012 |

OTHER PUBLICATIONS

International Search Report for PCT/KR2013/011803, English translation attached to original, Both completed by the Korean Patent Office on Jan. 7, 2014, All together 5 Pages.

*Primary Examiner* — Erika J Villaluna
(74) *Attorney, Agent, or Firm* — Brooks Kushman P.C.

(57) ABSTRACT

An embedded measurement device that is capable of measuring the component and a composition of a multi-phase flow fluid flowing in a pipe. The embedded measurement device includes: a high-pressure pipe tube in which the multi-phase flow fluid flows; a Raman probe that is partially inserted inside the high-pressure pipe tube and has an optical lens; and a Raman peak analysis unit that is connected to another part of the Raman probe. The device for measuring the composition of the multi-phase flow fluid measures a Raman peak intensity value of the multi-phase flow fluid in (Continued)

the high-pressure pipe tube by using the Raman probe, thereby determining the composition of the fluid.

14 Claims, 14 Drawing Sheets

(56) References Cited

U.S. PATENT DOCUMENTS

| | | |
|---|---|---|
| 7,385,692 B1 | 6/2008 | Nguyen |
| 2012/0070362 A1 | 3/2012 | Harms et al. |

EMBEDDED DEVICE FOR MEASURING COMPONENT AND COMPOSITION OF MULTI-PHASE FLOW FLUID FLOWING IN PIPE

CROSS-REFERENCE TO RELATED APPLICATION

This application is the U.S. national phase of PCT Application No. PCT/KR2013/011803 filed on Dec. 18, 2013, which claims priority to KR Patent Application No. 10-2012-0148961 filed on Dec. 18, 2012, the disclosures of which are incorporated in their entirety by reference herein.

TECHNICAL FIELD

The present invention relates to an embedded measuring device that is capable of measuring the components and composition of a multi-phase flowing fluid that flows within a pipe.

BACKGROUND ART

An offshore plant refers to production facilities that can collect marine resources (crude oil, gas, etc.) or produce target products using marine resources on or under the sea.

Generally, the majority of offshore plants are various types of marine facilities that are used to collect, produce and transport crude oil and natural gas. Recently, competition for the acquisition of subsea resources has been accelerated due to the depletion of onshore and inshore fossil fuel. A field that requires the highest technical capability among offshore plant industries is the field of subsea production and processing systems that process and produce crude oil, gas, etc. in subsea areas. For this reason, subsea production and processing systems have proved themselves to correspond to a higher value-added business.

In offshore plants including undersea plants, multi-phase flows formed of a combination of liquid, gas and solid phases are present in a process of transporting gas or oil as well as a process of producing gas or oil. That is, crude oil, gas, water, sand, mud, etc. located on the seabed are transported through the horizontal/vertical pipes of offshore plants. Such a multi-phase flowing fluid does not support smooth flow. In particular, at a specific pressure and temperature, gas and water are combined into a gas hydrate and thus cause plugging or blocking in a pipe, thereby resulting in a problem with the operation of an offshore plant.

Furthermore, multiple components are present even in the case of a single phase. For example, in a natural gas phase, multiple components, including methane, ethane and propane, are included. These components also considerably influence the flow and characteristics of a fluid.

In practice, when a problem with the flow of a multi-phase flowing fluid occurs in connection with the construction and operation of a floating offshore plant, it is difficult to determine the cause of the problem, the production rate decreases, and enormous expenses are required for recovery.

Accordingly, recently, research into the achievement of flow assurance through the analysis of the characteristics of a multi-phase flowing fluid and the detection of a pipe plugging problem in advance in processes of producing subsea resources and transporting the subsea resources to a marine platform has attracted a lot of attention. As part of the research, an apparatus in which a pipe arrangement capable of simulating an undersea environment in which multi-phase flow was performed was installed on the ground was proposed, and is referred to as a flow loop.

Actually, flow loops were installed and are being operated at the University of Tulsa in the U.S., SwRI in the U.S., IFP in France, SINTEF in Norway, and CSIRO in Australia.

Conventional flow loops or actual offshore plant facilities still remain at a level at which fluid characteristics, such as the pressure, temperature and flow rate of a multi-phase flowing fluid, are measured using measuring instruments and the formation of plugging or blocking attributable to the formation of a gas hydrate is visually observed via a monitoring window.

Meanwhile, even when an administrator is observing the inside of a pipe through the monitoring window at the time at which a hydrate starts to be generated within the pipe, it is nearly impossible to distinguish an initial hydrate and a simple particle from each other with the naked eye, and the time at which a plugging or blocking phenomenon can be dealt with can be considered to have been passed already if the hydrate has been so generated that they can be distinguished from each other.

In practice, when a plugging or blocking phenomenon has already occurred, a corresponding pipeline has been cut away conventionally. Although a reserve pipeline is installed in order to prepare for the cutting away of a pipeline, this cannot be considered to be a fundamental solution.

Currently, there is no method capable of detecting hydrate plugging in advance in a conventional flow loop apparatus or an offshore plant pipeline arrangement. The characteristics (temperature, pressure, and flow rate) of a multi-phase flowing fluid can be immediately measured, but a method of analyzing the composition of a multi-component fluid in real time is not present. For example, shorter-chain hydrocarbons composed of methane $CH_4$, ethane $C_2H_6$ and propane $C_3H_8$ are main components of natural gas, and longer-chain hydrocarbons ($C_6H_{14}$, $C_7H_{16}$, $C_8H_{18}$, etc.) are in a liquefied form and correspond to components of crude oil. In order to analyze these various components, a chromatography method (a gas or liquid chromatography method) of collecting a sample, separating each component from an analysis column and performing qualitative/quantitative analysis via various detectors (an FID, a TCD, and an MS) is generally best. However, these methods have critical disadvantages in that analysis is difficult to achieve, a measured sample must be discarded because the sample must be collected, and real-time analysis is impossible and also an excessively long analysis time is required because each component must be separated from a column and then analyzed by a detector. That is, it is impossible to individually and rapidly analyze various components in subsea offshore plant facilities or a flow loop using the existing conventional analysis method.

DISCLOSURE

Technical Problem

Accordingly, the present invention is intended to propose an embedded-type device for measuring the composition of a multi-phase flowing fluid, which has not yet been provided in conventional flow loops and conventional offshore plant fluid transfer facilities.

That is, the present invention is intended to propose a measuring device that determines the composition of multi-phase flowing components in real time and predicts a blocking phenomenon attributable to the formation of a hydrate in advance, thereby achieving the economical and efficient construction and operation of an offshore plant.

Technical Solution

In order to accomplish the above object, the present invention provides an embedded measuring device for measuring the components and composition of a multi-phase flowing fluid, including: a pipeline configured such that a multi-phase flowing fluid flows therethrough; a Raman probe configured such that a part thereof is inserted into the pipeline, and provided with an optical lens; and a Raman peak analysis unit connected to another part of the Raman probe; wherein the components and composition of the multi-phase flowing fluid are determined by measuring Raman peak intensity of the multi-phase flowing fluid within the pipeline using the Raman probe.

Preferably, the Raman probe includes one or more probes installed in the pipeline.

Preferably, the Raman probe includes: a first Raman probe installed in an upper portion of the pipeline; a second Raman probe installed in a lower portion of the pipeline; a third Raman probe installed in an upper portion of a curved part of the pipeline downstream of a fluid flow; and a fourth Raman probe installed in a lower portion of a curved part of the pipeline downstream of the fluid flow.

Preferably, the embedded measuring device determines the type of object of the formation of a gas hydrate, the speed of formation of each cavity and the speed of formation of the hydrate in real time by performing real-time Raman measurement in the pipeline using the Raman probe and while concurrently temperature and pressure.

Preferably, the Raman probe is compression-fitted into the pipeline.

Preferably, the Raman probe includes two or more different optical lenses in order to prevent chromatic aberration.

Preferably, the Raman probe includes a compression fitting Raman body compression-fitted into the pipeline; and a replaceable probe tip detachably coupled to the compression fitting Raman body, and configured to surround the two or more lenses.

Preferably, the Raman peak analysis unit determines the components and composition of the multi-phase flowing fluid by analyzing the Raman peak intensity and an intrinsic wavelength region measured by the Raman probe.

Preferably, the Raman peak analysis unit sets a calibration curve using a Raman peak intensity ratio of predetermined components and concentrations of the predetermined components, receives the Raman peak intensity measured using the Raman probe, and quantitatively analyzes components included in the multi-phase flowing fluid using the calibration curve.

Preferably, the Raman peak analysis unit determines the formation of a hydrate and the type of hydrate within the multi-phase flowing fluid by analyzing the Raman peak intensity and an intrinsic wavelength region measured by the Raman probe.

Preferably, the embedded measuring device further includes a pressure temperature control devices that operates when the Raman peak analysis unit detects the formation of the hydrate.

Preferably, the pressure temperature control device controls pressure and temperature within the pipeline so that they become different from phase equilibrium conditions for the hydrate being formed.

Preferably, the embedded measuring device further includes an inhibitor input device that operates when the Raman peak analysis unit detects the formation of the hydrate.

Preferably, the pipeline constitutes a flow loop.

Preferably, the embedded measuring device further includes a fluid supply unit configured to supply the multi-phase flowing fluid to the flow loop.

Preferably, the flow loop further includes a plurality of test units formed by making branches from the pipeline via valves.

Advantageous Effects

According to the present invention, it is possible to effectively determine the composition of a multi-phase flowing fluid in real time not only in a flow loop but also in an offshore plant.

Furthermore, the accuracy of measurement results can be considerably increased because intensity, rather than a Raman peak area value, is used.

In particular, the type and solubility (or liquefied components and composition) of gas included in a multi-phase flowing fluid can be precisely determined at a measurement location using Raman probes, and the determined data can be presented in a qualitative/quantitative manner.

Furthermore, a blocking phenomenon can be effectively predicted and prevented because the formation of a hydrate can be determined.

Furthermore, it is possible to precisely determine a Raman peak within a high-pressure pipe using compression fitting.

BEST MODE

Description of Measuring Device

A device for measuring the composition of a multi-phase flowing fluid according to the present invention will be described with reference to the drawings below.

Figure 1:
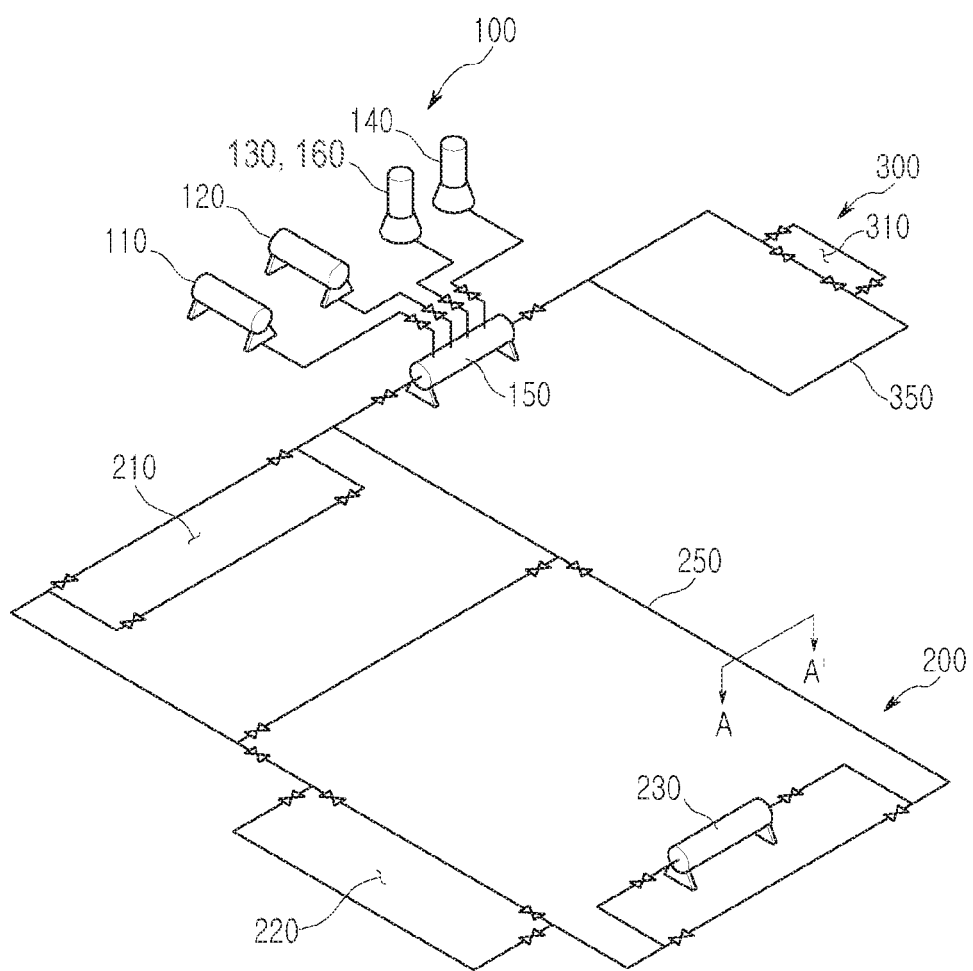
FIG. 1 schematically illustrates an embodiment of a flow loop according to the present invention.

FIG. 1 illustrates a flow loop according to the present invention.

The flow loop includes a fluid supply unit 100, a first flow loop 200, and a second flow loop 300.

The fluid supply unit 100 functions to supply a plurality of fluids for the implementation of an undersea multi-phase flowing fluid to the flow loops 200 and 300.

The fluid supply unit 100 includes a gas supply unit 110, an oil supply unit 120, a mixture supply unit 130, and a water supply unit 140, and supplies gas, oil, a mixture and water included in a undersea multi-phase flowing fluid.

Fluids generated therein form a multi-phase flowing fluid similar to an actual one while passing through a multi-phase flowing fluid generation unit 150, and the multi-phase flowing fluid is supplied to the flow loops 200 and 300.

In another embodiment not illustrated, a multi-phase flowing fluid actually extracted from the seabed may be supplied directly to the flow loops 200 and 300.

The flow loops 200 and 300 include a plurality of high-pressure pipelines 250 and 350, and have a structure in which an internal multi-phase flowing fluid is circulated therethrough.

Furthermore, the high-pressure pipelines 250 and 350 must sufficiently withstand high-pressure and low-temperature conditions, i.e., the undersea conditions of a multi-phase flowing fluid.

The first flow loop 200 and the second flow loop 300 have similar structures but different sizes, and thus may be used for various purposes.

Although the sizes of the length and width of the second flow loop 300 are halves of those of the first flow loop 200 in the illustrated embodiment, it will be apparent that the sizes are not limited thereto.

A plurality of test units 210, 220 and 310 is located in the flow loops 200 and 300.

A plurality of valves is located at the front and back ends of the test units 210, 220 and 310, and branches are made from the main streams of the flow loops 200 and 300, as illustrated in the drawing.

The valves may control whether to allow a multi-phase flowing fluid to flow into the test units 210, 220 and 310 in accordance with separate measuring purposes without affecting main streams.

Furthermore, a separate separator 230 is located, and thus a multi-phase flowing fluid is separated within a flow loop, which is used for testing purposes.

Figure 2:
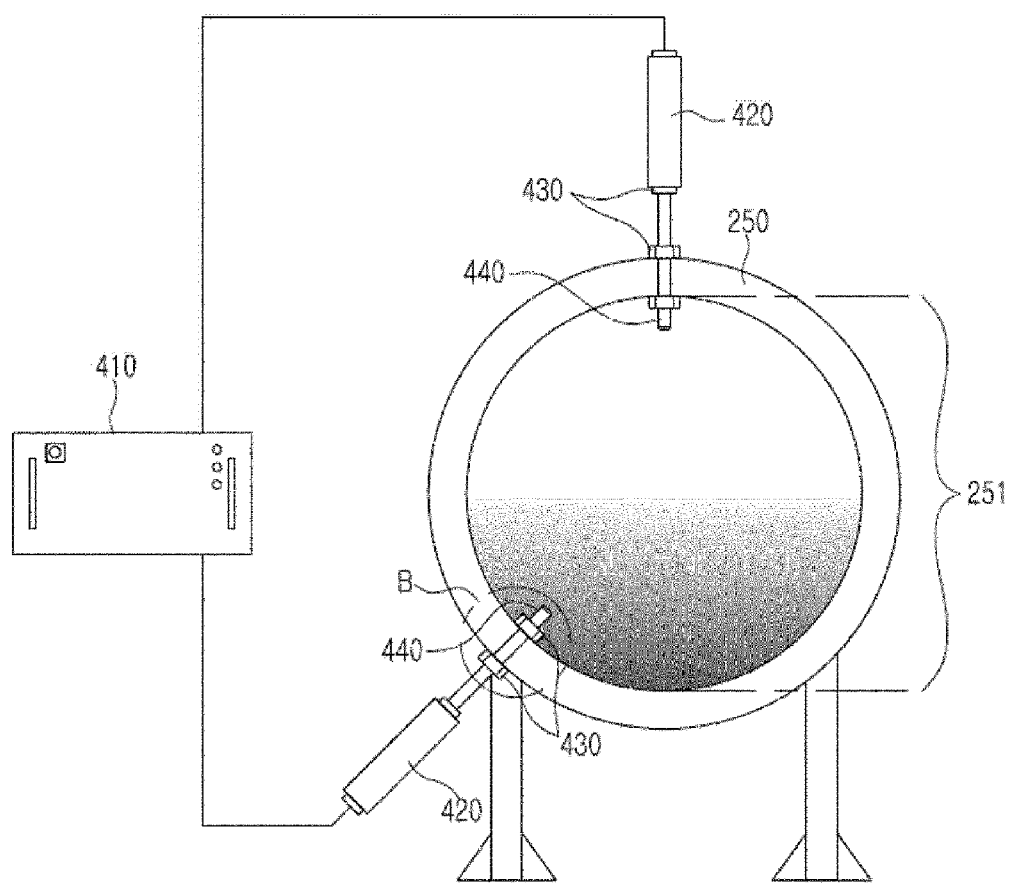
FIG. 2 is a sectional view taken along line A-A' of FIG. 1, and illustrates, in detail, a Raman probe installed in a flow loop according to the present invention.

The high-pressure pipeline 250 is described in detail with reference to FIG. 2.

A Raman probe 440 is installed in the high-pressure pipeline 250.

More specifically, a part of the Raman probe 440 is inserted into the high-pressure pipeline 250, another part thereof protrudes to the outside, and still another part thereof is connected to a Raman peak analysis unit 410 through a Raman body 420.

Since the inside of the high-pressure pipeline 250 is in an atmosphere of high pressure and low temperature, the insertion of the Raman probe 440 is a process that requires relatively careful attention.

For this purpose, the Raman probe 440 must be installed into the high-pressure pipeline 250 in a compression fitting manner, and then the Raman probe 440 must be fastened by separate fastening members 430 and 444 outside and inside of the high-pressure pipeline 250.

Furthermore, it is preferred that two Raman probes 440 form a set and are installed in the upper and lower portions of the high-pressure pipeline 250, respectively (first and second Raman probes).

By doing so, the Raman probe 440 installed in the upper portion may determines the Raman peak intensity of a gas-based multi-phase flowing fluid chiefly located in the upper portion of the inside of the high-pressure pipeline 250, and the Raman probe 440 installed in the lower portion may determine the Raman peak intensity of a liquid-based multi-phase flowing fluid chiefly located in the lower portion of the inside of the high-pressure pipeline 250.

Additionally, it is preferred that another set of Raman probes 440 different from the above-described set of two probes are installed in the upper and lower portions of the pipeline 250, respectively, in the downstream of a fluid flow (third and fourth Raman probes).

Using this, a measurement error that may occur because the first and second Raman probes resist a fluid flow can be prevented, and the accuracy of a result can be increased.

Figure 3A:
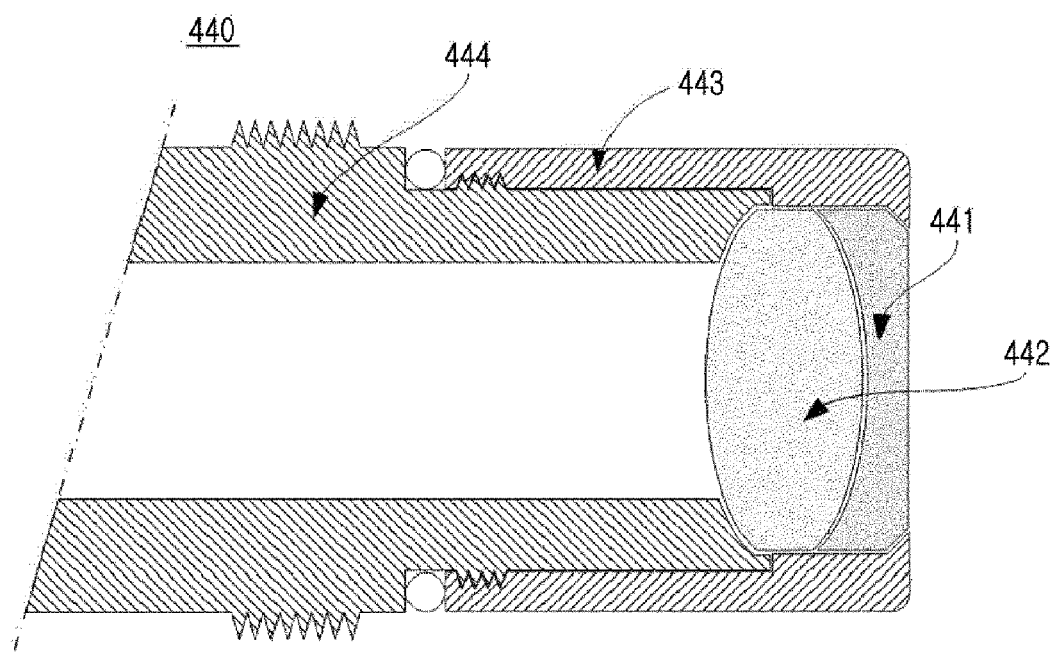
FIG. 3a is a detailed view of portion B of FIG. 2, and illustrates, in detail, a Raman probe installed in a flow loop according to the present invention.
Figure 3B:
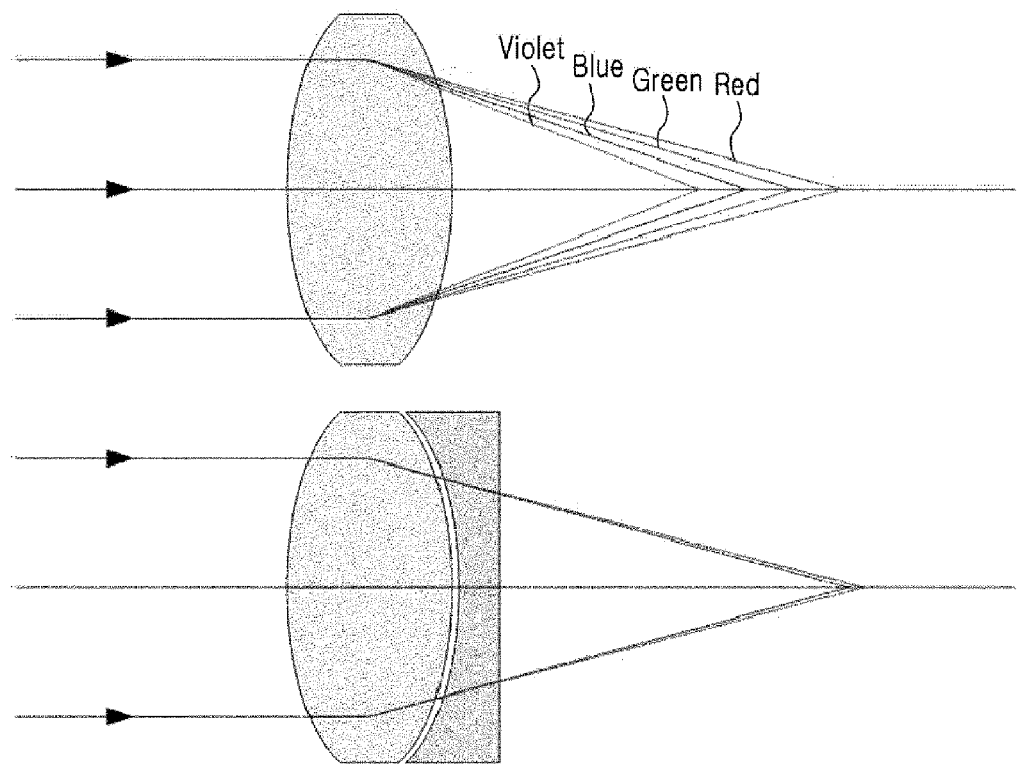
FIG. 3b is a diagram illustrating two or more lenses intended to prevent chromatic aberration in a Raman probe.

The Raman probe 440 is described in greater detail with reference to FIGS. 3a and 3b.

The Raman probe 440 includes two or more optical lenses 441 and 442. The two or more optical lenses 441 and 442 may be superimposed on each other so that wavelength light scattered variously can converge after laser light has been radiated onto a sample. Using this, the focal distance between red and violet is reduced, so that chromatic aberration can be reduced and the accuracy of measurement can be increased. Using this, in a multi-phase flow environment, precise data Raman analysis can be made. In this case, the term "Raman analysis" refers to the analysis of the components and composition of a multi-phase flowing fluid using Raman peak intensity.

Furthermore, the Raman probe 440 may further include a compression fitting Raman body 444 compression-fitted into the high-pressure pipeline 250 or 350, and a replaceable probe tip 443 detachably coupled to the compression fitting Raman body 444 while surrounding the two or more optical lenses 441 and 442.

The reason for this is that in the environment of high-pressure pipelines 250 and 350 in which only the outside lens 442 of the Raman probe 440 is in a high-pressure state, contact with a multi-phase flowing fluid frequently occurs and thus frequent contamination and abrasion phenomena frequently occur, in which case easy replacement is attempted to be replaced.

Meanwhile, the Raman peak analysis unit 410 may receive various types of information about a Raman peak via the Raman probes 440, and may determine the components and composition, such as the type and solubility, of gases included in a corresponding multi-phase flowing fluid via the received information.

Furthermore, the pressures and temperatures of the high-pressure pipelines 250 and 350 may be measured using separate sensors (not illustrated) in real time, and may be controlled via a pressure temperature control device 510 as desired.

Meanwhile, each of the high-pressure pipelines 250 and 350 may further include an inhibitor input device 160. This inhibitor input device is operated when the formation of a hydrate is detected in each of the high-pressure pipelines 250 and 350, thereby suppressing the formation of a hydrate and thus preventing a plugging or blocking phenomenon.

Description of Measuring Method

A method of measuring the component and composition of a multi-phase flowing fluid according to the present invention is described with reference to FIGS. 1, 3 and 7.

A multi-phase flowing fluid generated by the fluid supply unit 100 or a multi-phase flowing fluid extracted from a seabed is supplied to the flow loops 200 and 300.

The multi-phase flowing fluid is circulated through the flow loops 200 and 300, in which process separate tests may be conducted using separate measuring devices at the test units 210, 220 and 310.

Meanwhile, when the Raman probe 440 located in each of the high-pressure pipelines 250 and 350 of flow loops 200 and 300 is operated, various types of Raman peak-related information is determined via optical lenses 441 and 442, and is transferred to the Raman peak analysis unit 410.

The Raman peak analysis unit 410 may determine the component and composition of the multi-phase flowing fluid at a corresponding location using the received various types of Raman peak-related information.

Although information about the multi-phase flowing fluid determined via the Raman peak information includes the type of gas included in the multi-phase flowing fluid, the solubility of the corresponding gas, the components and composition of liquids, the formation and type of a hydrate and its components and composition, the present invention is not limited thereto.

If, as a result of the determination by the Raman peak analysis unit 410, it is determined that a hydrate is forming in a corresponding pipe, it is preferred to suppress the formation.

For this purpose, in an embodiment, phase equilibrium conditions based on the type of hydrate may be determined and then a pressure temperature control device 510 may change phase equilibrium conditions.

In another embodiment, an inhibitor input device 160 capable of suppressing the formation of a hydrate may input inhibitor to each of the high-pressure pipelines 250 and 350.

Composition Measurement Examples (Qualitative and Quantitative Component and Composition Analysis)

A plurality of examples in which the components and composition of a multi-phase flowing fluid are measured using a measuring device according to the present invention is described below.

Via the present examples, whether a change in component and composition that influences the formation and dissociation of a gas hydrate in a multi-phase flowing fluid can be measured through real-time Raman peak analysis is determined.

Figure 4A:
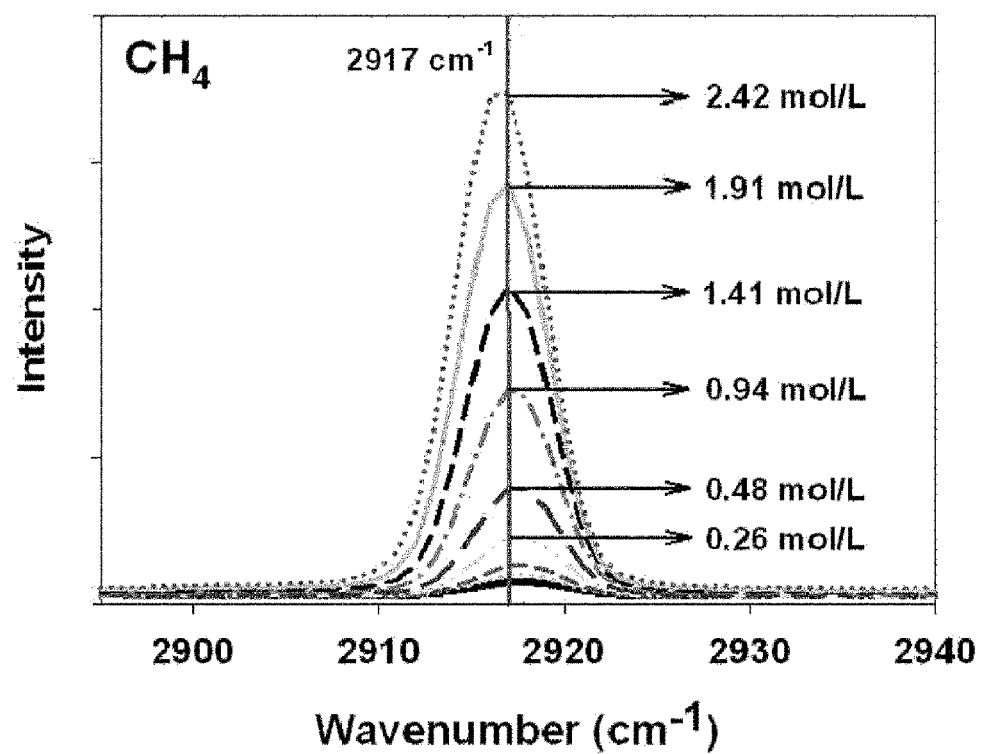
FIGS. 4a and 4b illustrate examples in which the components and composition of a flowing fluid were measured using a measuring device according to the present invention, and plot Raman analysis values according to pressure in single gases of methane and ethane on graphs.

First Example (FIG. 4a)

A methane gas was injected into the multi-phase flowing fluid generation unit 150 formed of a high-pressure container, a high-pressure condition was formed, and then the methane gas was allowed to flow through the high-pressure pipelines 250 and 350. The high-pressure pipelines 250 and 350 and the multi-phase flowing fluid generation unit 150 were programmed such that temperature and pressure data could be monitored in real time, as illustrated in FIG. 7, and were maintained at 10° C. by cooling water.

The intensity of a Raman peak was measured using the Raman probes 440 inserted into the high-pressure pipelines 250 and 350. Although an experimenter had freely selected and used one of a Raman peak area and an intensity measurement value without specific distinction therebetween in the conventional technology, the Raman peak intensity was measured based on accuracy in the present example. This will be described later.

This experiment was conducted a few times while the pressure of methane, i.e., a target gas, was being changed from 0.1 to 50 bar.

Experiment results are illustrated in FIG. 4a, and are analyzed, as follows.

Methane exhibited an increase according to pressure at $2917\ cm^{-1}$, i.e., a carbon and hydrogen bonding symmetric stretching peak. Accordingly, it could be determined by examining only a Raman peak wavelength measurement region illustrated in FIG. 4a that a methane gas was included in the multi-phase flowing fluid.

Furthermore, as illustrated in the drawing, the number of moles of a corresponding gas could be determined via the intensity of a measured Raman peak. The reason for this is that the number of moles increases at the same ratio as pressure increases.

Figure 4B:
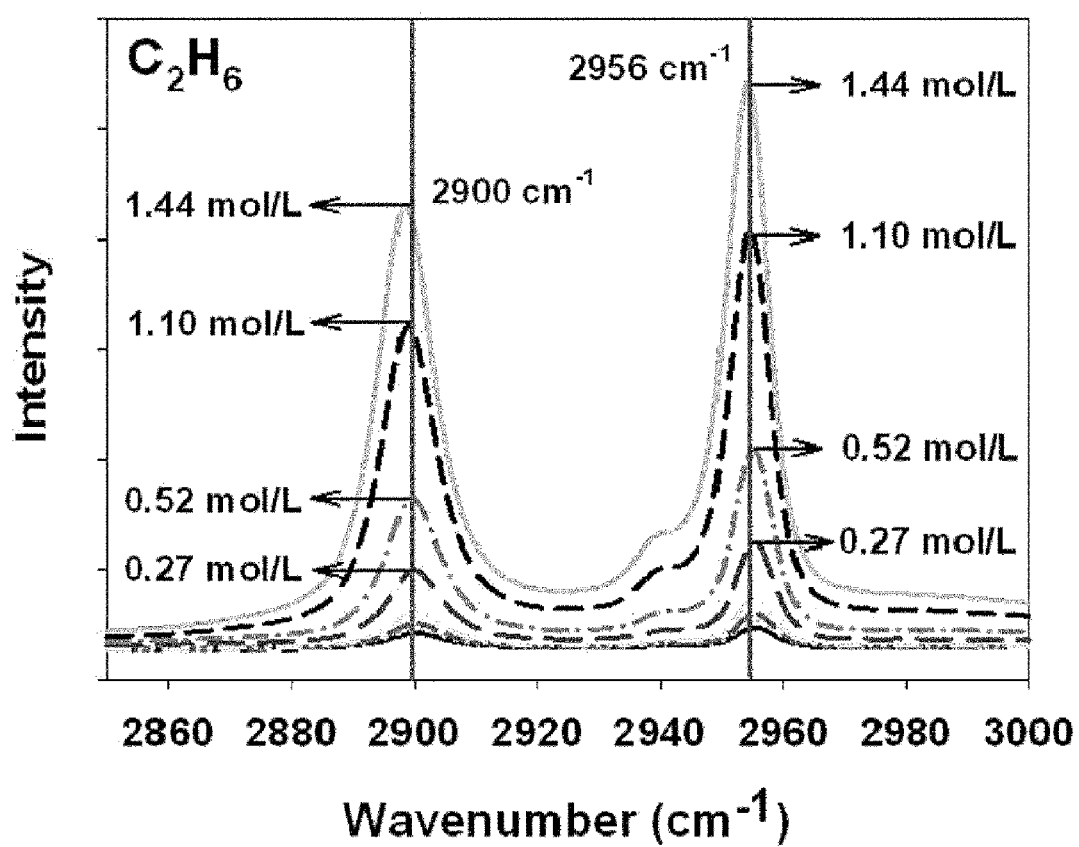

Second Example (FIG. 4b)

In the second example, ethane gas was used instead of methane.

Experiment results were illustrated in FIG. 4b, and were analyzed, as follows.

Generally, ethane exhibited an increase according to pressure at $2900\ cm^{-1}$ and $2956\ cm^{-1}$, i.e., carbon and hydrogen bonding bending peaks. Accordingly, it could be determined by examining only wavelength measurement results regarding Raman peak intensity illustrated in FIG. 4b that an ethane gas was included in a multi-phase flowing fluid.

Furthermore, as illustrated in the drawing, the number of moles of a corresponding gas could be determined via the intensity of a measured Raman peak.

Figure 5:
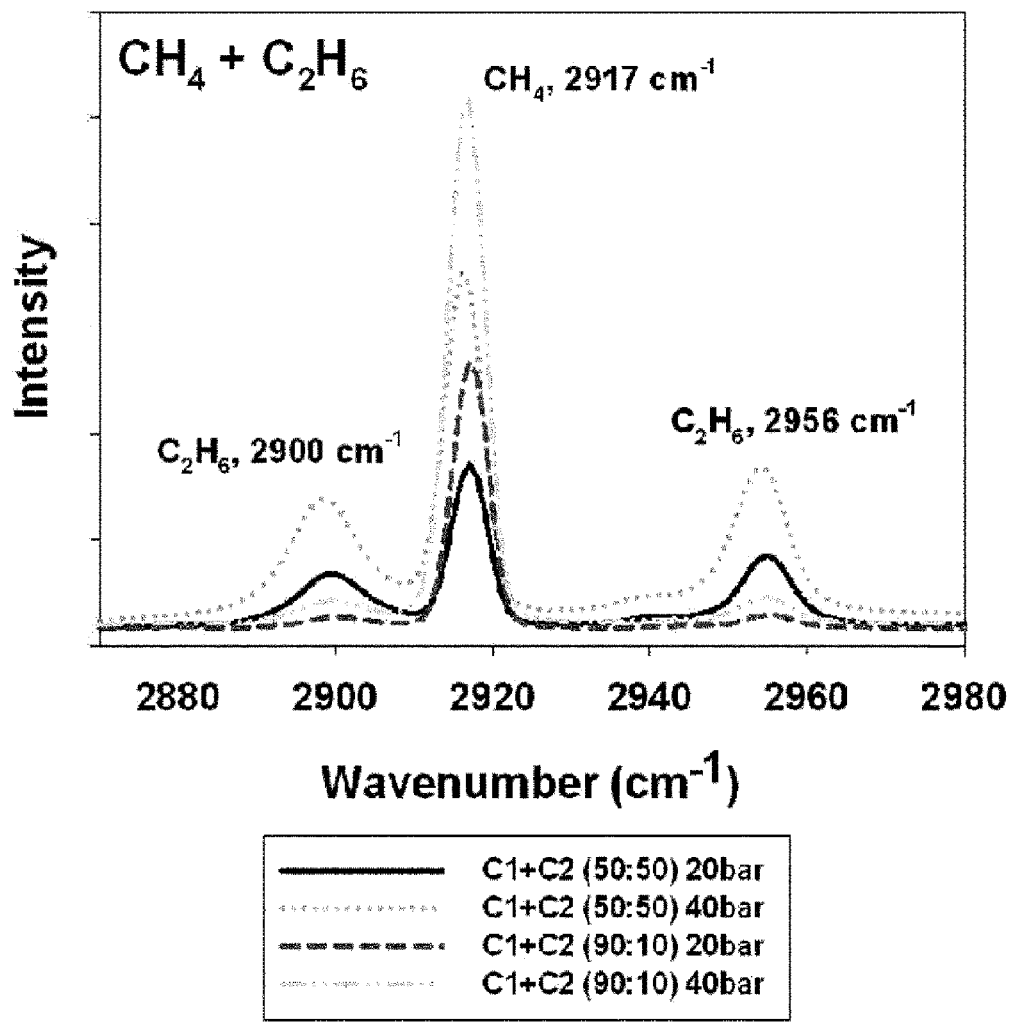
FIG. 5 plots actually measured Raman analysis values according to pressure on a graph when methane and ethane used in connection with FIG. 4 are mixed into composite gases at ratios of 90:10(%) and 50:50(%)

Third Example (FIG. 5)

Unlike the first and second examples, methane and ethane were used at the ratios of 9:1(%) and 5:5(%) as target gases.

Furthermore, Raman peak intensities were measured in two pressure conditions of 20 and 40 bar.

Experimental results are illustrated in FIG. 5, and are analyzed as follows.

The composite gases exhibited an increase according to pressure at $2917\ cm^{-1}$, i.e., the carbon and hydrogen bonding symmetric stretching peak of methane, and at $2900\ cm^{-1}$ and $2956\ cm^{-1}$, i.e., the carbon and hydrogen bonding bending peaks of ethane, which were the same as the locations of the single gases. Accordingly, it could be determined by examining only measurement results illustrated in FIG. 5 that both methane and ethane were included in a multi-phase flowing fluid.

Meanwhile, when the Raman peak intensities of the composite gases having two ratios were compared with each other in the same pressure condition, the Raman peak intensities increased at almost the same ratio as pressure increased in the same manner as in the case of the single gases.

This is an example that directly indicates that the qualitative and quantitative analysis of a single or composite gas can be made using only Raman analysis without an existing chromatography method.

Fourth Example—Comparison Between Raman Peak Area Value Measurement and Intensity Measurement (FIGS. 6a to 6d)

A calibration curve was plotted according to the number of moles based on the peak intensities and area values of methane and ethane single gases according to pressure, and is illustrated in FIG. 6.

The numbers of moles of each of the analyzed methane and ethane gases were calculated based on the measured results of the Raman analysis.

As a result of the calculation, as illustrated in FIGS. 6a to 6d, the Raman peak intensity increased at a substantially similar ratio as the pressure of the methane or ethane single gas increased, which exhibited linearity close to 1.

The methane exhibited such a tendency at 2917 cm$^{-1}$, i.e., a carbon and hydrogen bonding symmetric stretching peak, and the ethane exhibited the same tendency at 2900 cm$^{-1}$ and 2956 cm$^{-1}$, i.e., carbon and hydrogen bonding bending peaks.

In the present experiment, the Raman peak intensity exhibited a more accurate measurement value than the peak area value in microanalysis. This can be verified via FIG. 6d.

Figure 6A:
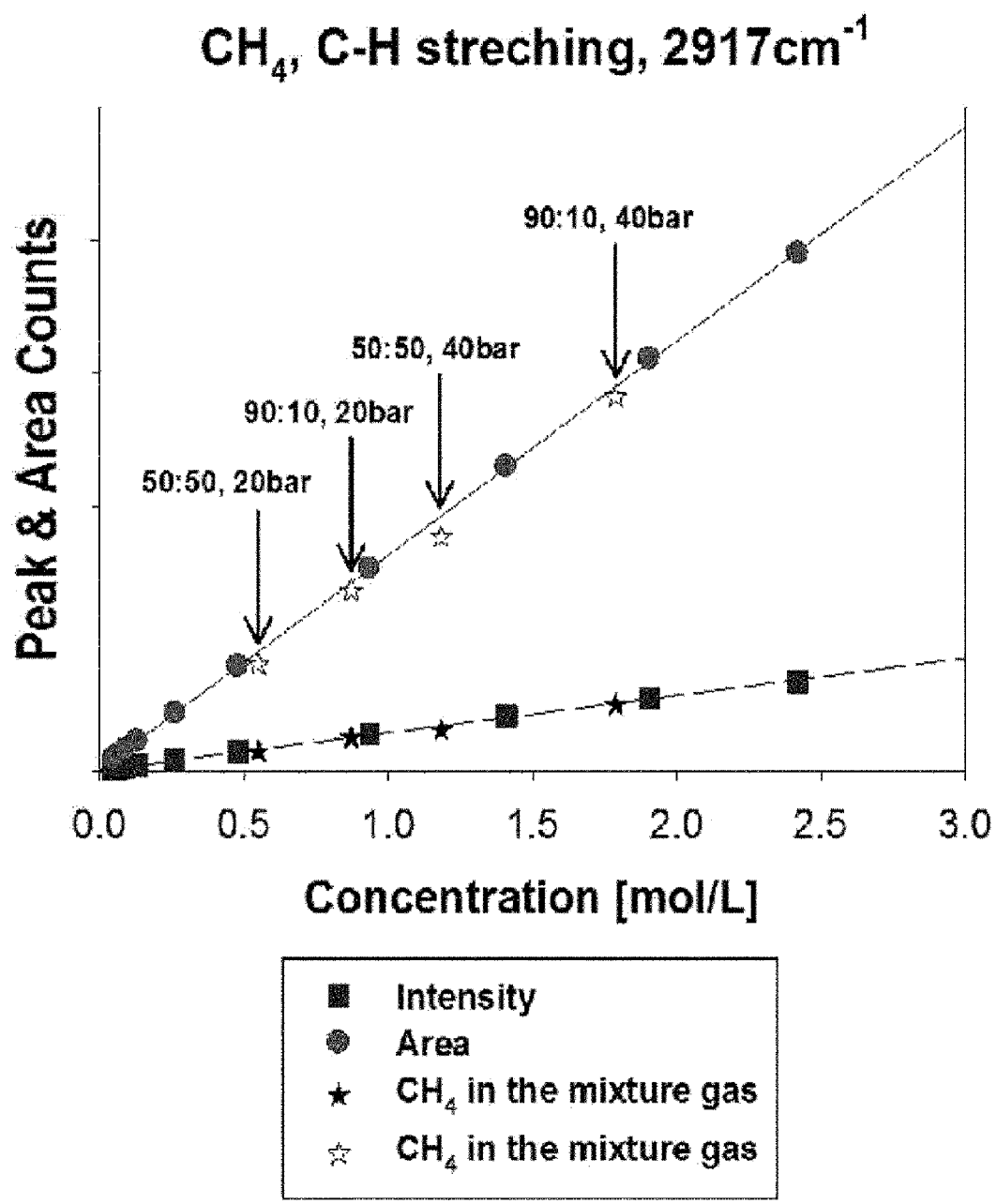
FIGS. 6a to 6d plot the tendencies of each gas of methane and ethane according to pressure, calculated in the numbers of moles, on graphs.
Figure 6B:
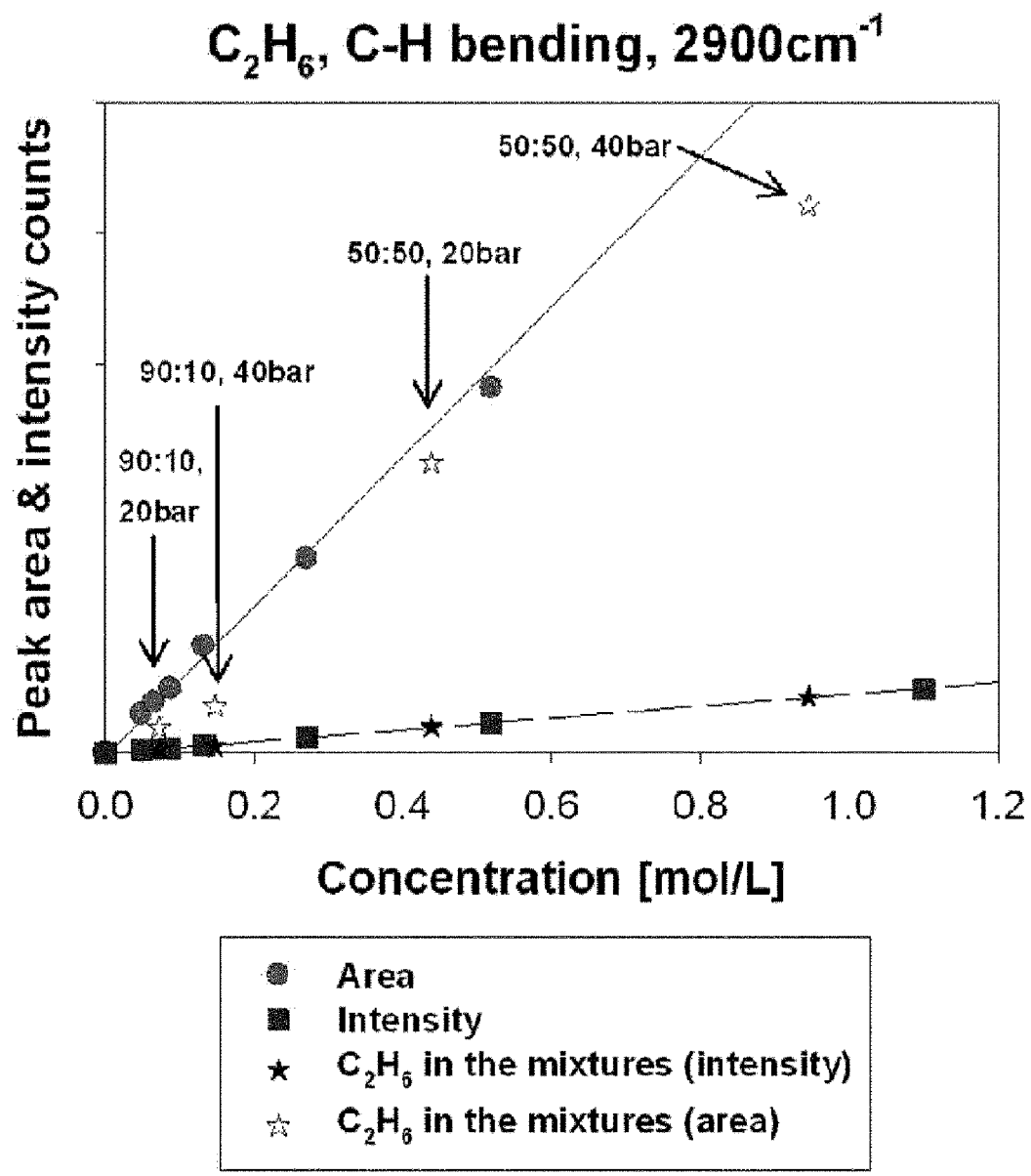
Figure 6C:
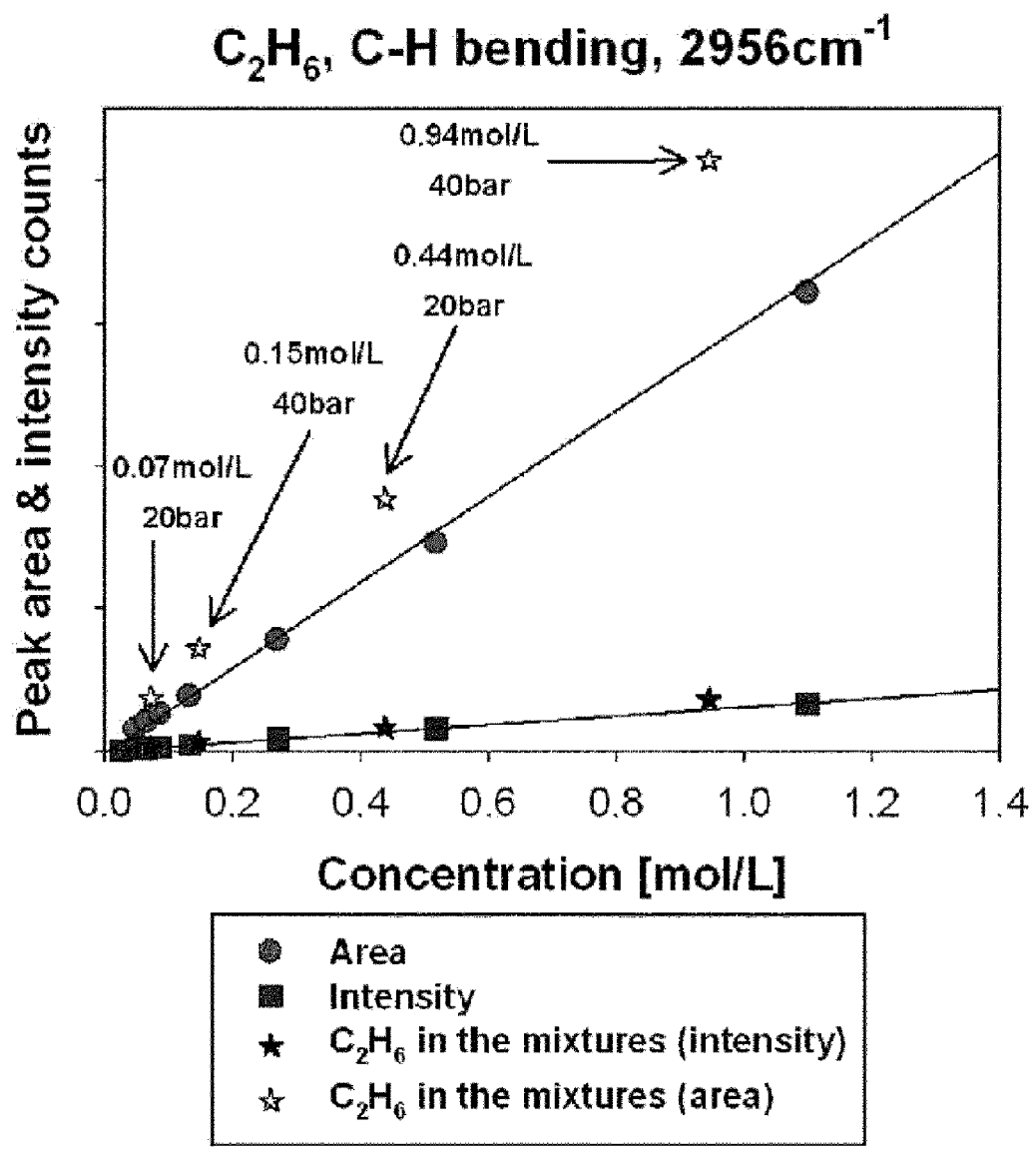
Figure 6D:
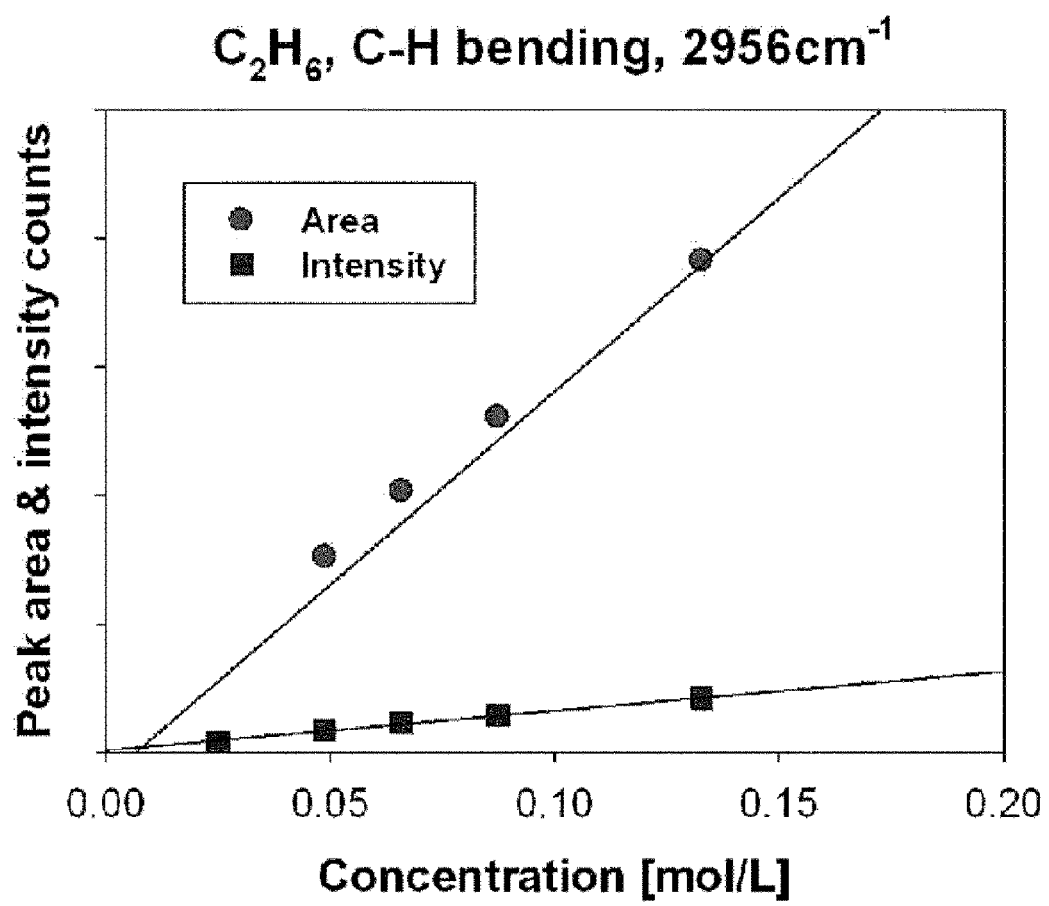

* As illustrated in FIG. 6d, in the case of the ethane, it was observed that the accuracy of the carbon and hydrogen bonding bending-related Raman peak area value was low in component analysis in a range equal to or lower than 0.1 mol/L and furthermore a peak area was not distinguished from a baseline in a range equal to or lower than 0.05 mol/L.

In contrast, the Raman peak intensity exhibited an almost rectilinear calibration curve in a range equal to or lower than 0.1 mol/L, and a minimum detection level exhibited the result of reaching a value equal to or lower than about 0.025 mol/L (although microanalysis result values related to the methane are not illustrated, the peak intensity exhibited more accurate measurement values and more desirable minimum detection levels than the peak area in microanalysis, like in the case of the ethane).

Accordingly, it is verified that according to the present invention, the components and composition of a multi-phase flowing fluid can be considerably accurately measured via the results of the measurement using the Raman peak intensity rather than the Raman peak area value.

This verifies that the relative analysis accuracy of the peak size is high in the conditions of a turbulent flow and a multi-phase flow or in a condition in which a target component has a low concentration and thus is more useful.

Gas Hydrate Measurement Example

Figure 7:
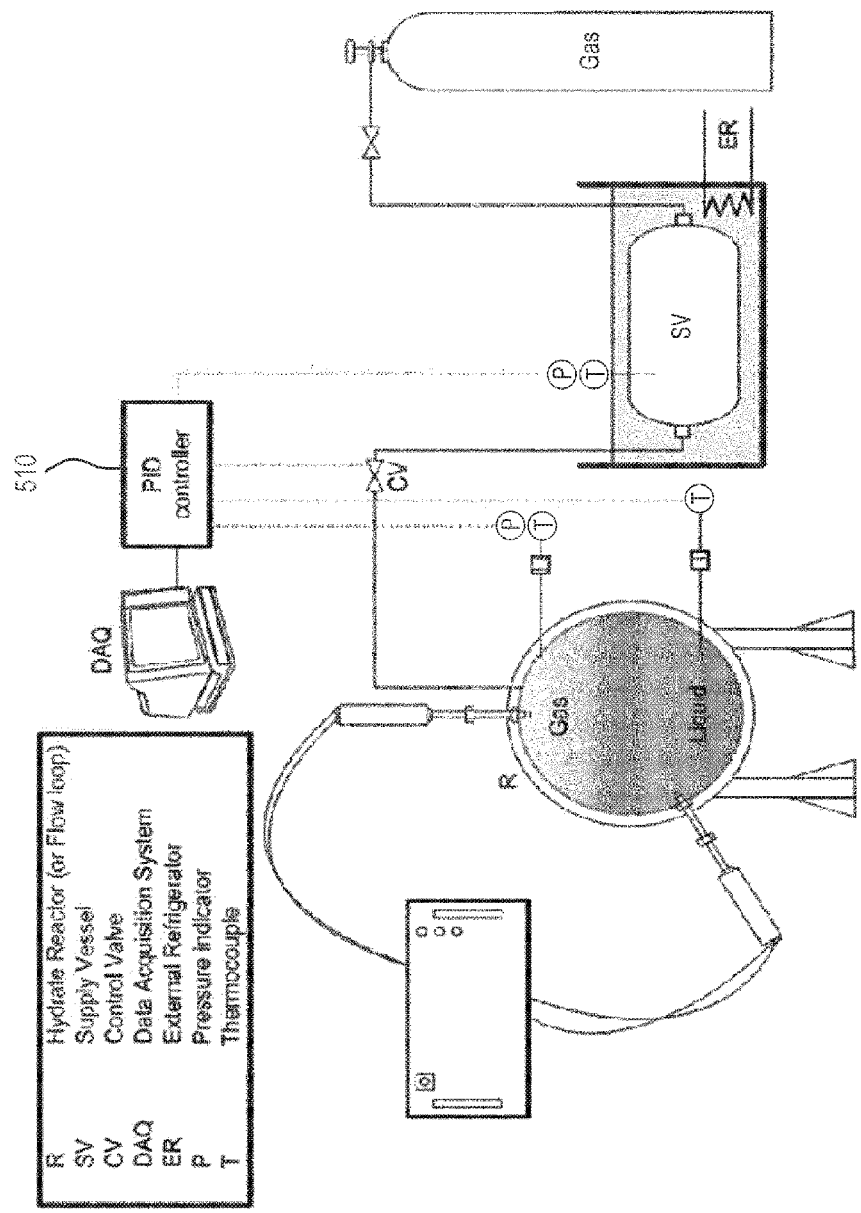
FIG. 7 illustrates an apparatus that was used to obtain the experimental results of FIGS. 4 to 6.

FIG. 7 schematically illustrates the configuration of a hydrate formation system in the high-pressure pipeline 250 or 350 of each of the actual flow loops.

The present system is systemized to maintain and control desired temperature and pressure, and is programmed to monitor temperature and pressure data in real time in a flowing situation.

Furthermore, the outside of the apparatus is configured in the form of a jacket, and is configured to maintain desired temperature using cooling water.

A guest gas used in actual measurement was a methane gas. Raman probes were installed through the high-pressure wall of the apparatus, i.e., the gaseous and liquefied jacket, in constant-temperature/constant-pressure and flowing conditions, and were allowed to predict molecular behavior via real time Raman measurement by measuring a change in the composition of an internal gaseous/liquefied phase and the formation of a hydrate.

Figure 8:
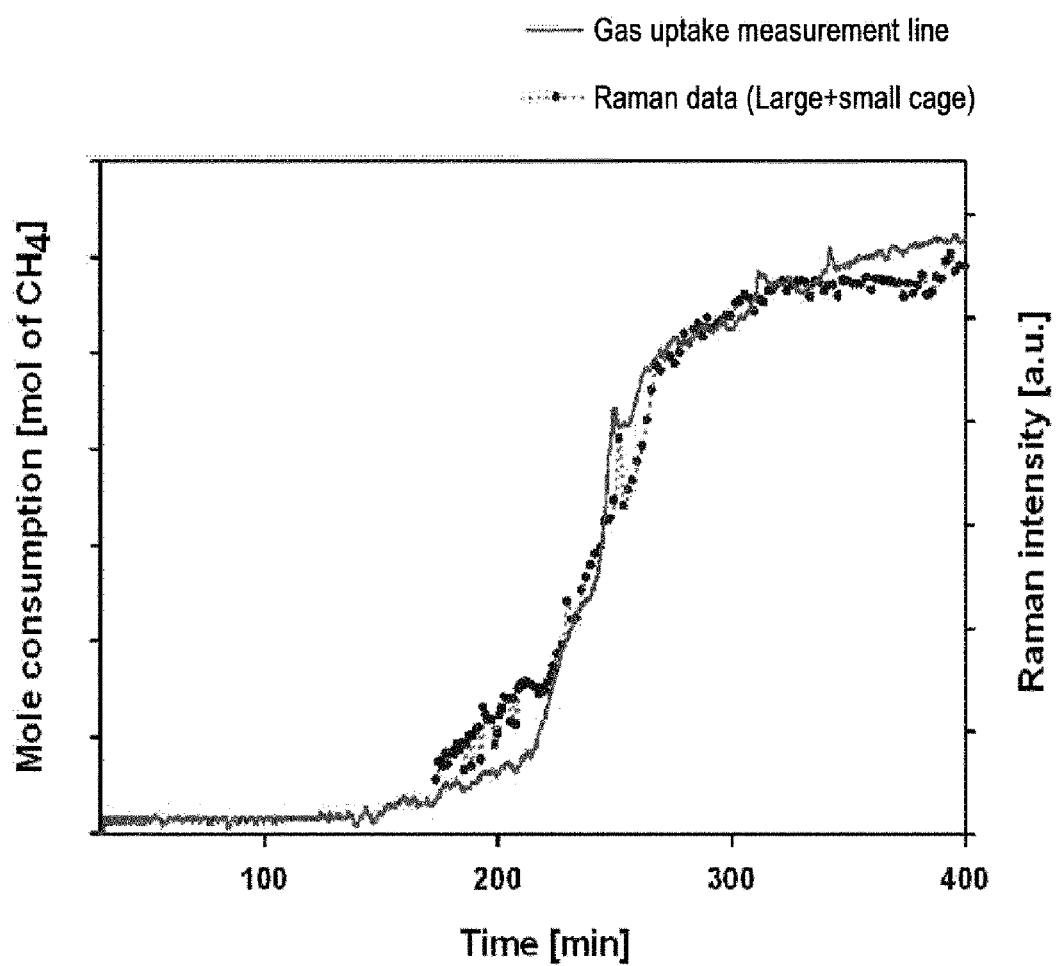
FIG. 8 illustrates values that are obtained by simultaneously comparing the speeds of formation of a hydrate over time with micro-level molecular behavior based on real-time Raman analysis in a flow loop.

FIG. 8 is a graph on which a methane hydrate formation speed curve and real-time Raman peak information are simultaneously measured and plotted.

As illustrated in FIG. 8, up to about 180 minutes, there was no change in the amount of gas consumption and also information about a methane hydrate peak did not appear in a Raman signal.

However, after about 180 minutes, it was observed that the amount of methane gas consumption gradually increased and also the Raman intensity of a methane hydrate large cavity (2905 cm$^{-1}$) and the Raman intensity of a methane hydrate small cavity (2915 cm$^{-1}$) were measured.

Furthermore, it can be seen that, when a methane gas uptake measurement line was compared with changes in the intensity of a methane hydrate Raman peak (the sum of the Raman peaks of large and small cavities), they had considerably similar forms.

This means that the formation of a hydrate, the speed of formation of the hydrate over time and molecular behavior in a multi-phase flowing fluid can be sufficiently predicted using only real-time Raman peak information based on real-time Raman intensity in a high-pressure flow loop formation system.

Figure 9:
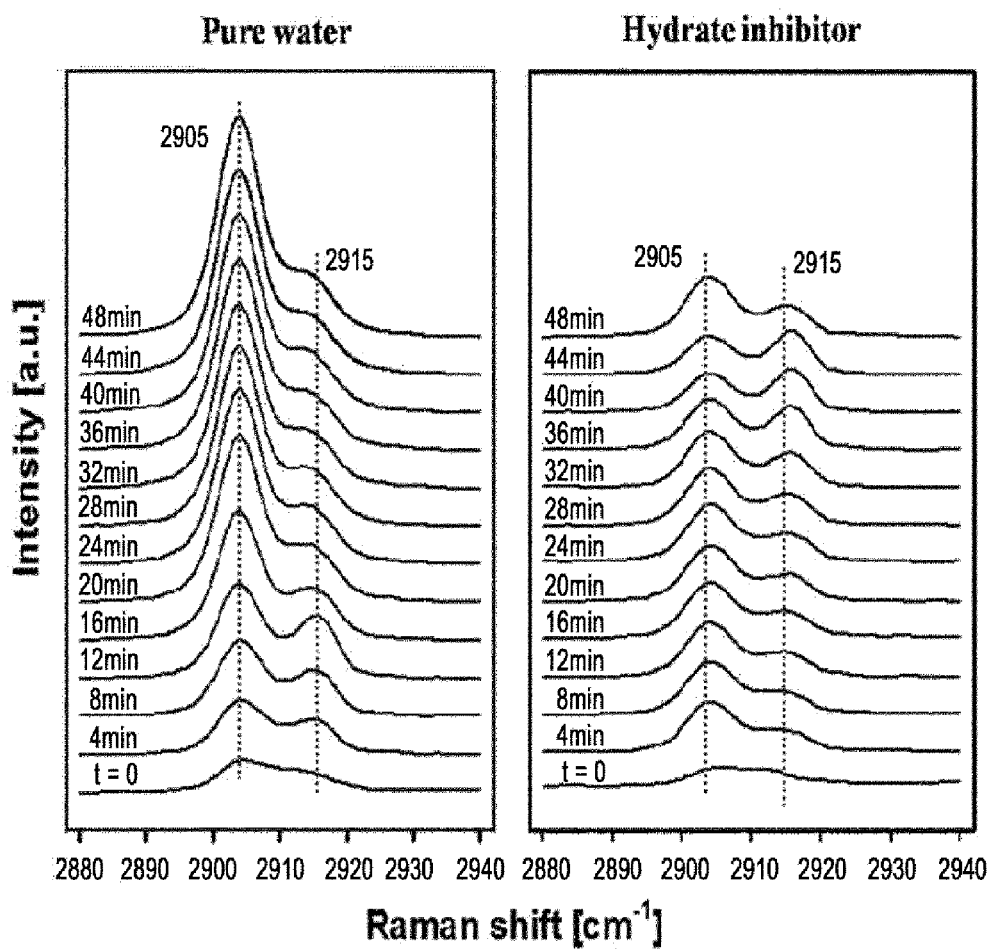
FIG. 9 compares and illustrates, in real time, Raman peaks that are formed in connection with the input of pure water and an inhibitor in Raman analysis.

FIG. 9 illustrates real-time Raman peak information based on the formation of a methane hydrate, and indicates that pure water and inhibitor capable of suppressing the formation of a hydrate were injected into the apparatus and Raman peak information about a hydrate formation step was acquired under constant temperature and pressure conditions at intervals of four minutes through Raman measurement in real time.

Referring to Raman measurement data based on two types of experimental results, the time at which the nucleus of a methane hydrate was formed could be clearly identified based on the peak shape and the wavelength.

In the case of a methane hydrate, the wavelengths of large and small cavities appeared at 2905 cm$^{-1}$ and 2915 cm$^{-1}$, and values could be acquired by measuring the peak intensity and the peak area.

The pure water exhibited the Raman peak shape of a general methane hydrate (a filling ratio between large and small cavities) attributable to the formation of a methane hydrate. In contrast, referring to Raman peak information in the case where an inhibitor was injected, it could be seen via the Raman peak intensity that an initial hydrate nucleus formation step was considerably delayed.

Furthermore, when the filling ratio between the large and small cavities of a methane hydrate based on the peak intensity and the peak area value was compared with that of pure water as the hydrate formed, it was observed that a significant difference in peak intensity appeared at a methane hydrate nucleus formation step and this could be clearly identified even with the naked eye via a monitoring window.

In the same manner, the composition of the multi-phase flowing fluid and the formation and type of a hydrate in the multi-phase flowing fluid could be acquired using the real-time Raman peak information, and also molecular-level information could be acquired via the Raman peak value.

Although the preferred embodiments of the present invention have been described above, the present invention is not limited to the above-described specific embodiments. That is, those having ordinary knowledge in a technical field to which the present invention pertains can make a plurality of variations and modifications to the present invention without departing from the spirit and scope of the attached claims, and equivalents to all such appropriate variations and modifications should be considered to fall within the scope of the present invention.

The invention claimed is:

1. An embedded measuring device for measuring components and composition of a multi-phase flowing fluid, comprising:
   a pipeline configured such that a multi-phase flowing fluid flows therethrough;
   a Raman probe configured such that a part thereof is inserted into the pipeline, and provided with an optical lens; and
   a Raman peak analysis unit connected to another part of the Raman probe;

wherein the Raman probe comprises:
a compression fitting Raman body compression-fitted into the pipeline; and
a replaceable probe tip detachably coupled to the compression fitting Raman body; and
wherein components and composition of the multi-phase flowing fluid are determined by measuring Raman peak intensity of the multi-phase flowing fluid within the pipeline using the Raman probe.

2. The embedded measuring device of claim 1, wherein the Raman probe further comprises an optical lens for preventing chromatic aberration, and the replaceable probe tip surrounds the optical lens.

3. The embedded measuring device of claim 2, wherein the Raman probe comprises one or more probes installed in the pipeline.

4. The embedded measuring device of claim 3, wherein the Raman probe comprises:
a first Raman probe installed in an upper portion of the pipeline; and
a second Raman probe installed in a lower portion of the pipeline.

5. The embedded measuring device of claim 1, wherein the embedded measuring device determines a type of a gas-hydrate forming object, a speed of formation of each cavity, and a speed of formation of the hydrate in real time by performing real-time Raman measurement in the pipeline using the Raman probe while concurrently measuring temperature and pressure.

6. The embedded measuring device of claim 1, wherein the Raman peak analysis unit determines the components and composition of the multi-phase flowing fluid by analyzing the Raman peak intensity and an intrinsic wavelength region measured by the Raman probe.

7. The embedded measuring device of claim 6, wherein the Raman peak analysis unit:

sets a calibration curve using a Raman peak intensity ratio of predetermined components and concentrations of the predetermined components;
receives the Raman peak intensity measured using the Raman probe; and
quantitatively analyzes components included in the multi-phase flowing fluid using the calibration curve.

8. The embedded measuring device of claim 6, wherein the Raman peak analysis unit determines formation of a hydrate and a type of hydrate within the multi-phase flowing fluid by analyzing the Raman peak intensity and an intrinsic wavelength region measured by the Raman probe.

9. The embedded measuring device of claim 8, wherein the embedded measuring device further comprises a pressure temperature control devices that operates when the Raman peak analysis unit detects the formation of the hydrate.

10. The embedded measuring device of claim 9, wherein the pressure temperature control device controls pressure and temperature within the pipeline so that they become different from phase equilibrium conditions for the hydrate being formed.

11. The embedded measuring device of claim 8, wherein the embedded measuring device further comprises an inhibitor input device that operates when the Raman peak analysis unit detects the formation of the hydrate.

12. The embedded measuring device of claim 1, wherein the pipeline constitutes a part of a flow loop or pipeline that transports a multi-phase flowing fluid of petroleum, or natural gas.

13. The embedded measuring device of claim 12, further comprising a fluid supply unit configured to supply the multi-phase flowing fluid to the flow loop or pipeline.

14. The embedded measuring device of claim 13, wherein the flow loop or pipeline further comprises a plurality of test units formed by making branches from the pipeline via valves.

* * * * *